United States Patent
Wiley

[11] Patent Number: 5,980,558
[45] Date of Patent: Nov. 9, 1999

[54] SUTURE ANCHOR SYSTEM

[75] Inventor: Roy C. Wiley, Warsaw, Ind.

[73] Assignee: Biomet Inc., Warsaw, Ind.

[21] Appl. No.: 08/941,405

[22] Filed: Sep. 30, 1997

[51] Int. Cl.[6] .................................................. A61B 17/04
[52] U.S. Cl. ........................................ 606/232; 606/104
[58] Field of Search ...................................... 606/104, 232

[56] References Cited

U.S. PATENT DOCUMENTS

| | | | |
|---|---|---|---|
| 552,284 | 12/1895 | Greaves et al. | 606/232 |
| 4,741,330 | 5/1988 | Hayhurst | 606/232 |
| 4,898,156 | 2/1990 | Gautturna et al. | 606/232 |
| 4,899,743 | 2/1990 | Nicholson et al. | 606/232 |
| 4,968,315 | 11/1990 | Gatturna | 606/232 |
| 5,037,422 | 8/1991 | Hayhurst et al. | 606/232 |
| 5,141,520 | 8/1992 | Goble et al. | 606/232 |
| 5,192,303 | 3/1993 | Gatturna et al. | 606/232 |
| 5,217,486 | 6/1993 | Rice et al. | 606/232 |
| 5,224,946 | 7/1993 | Hayhurst et al. | 606/232 |
| 5,236,445 | 8/1993 | Hayhurst et al. | 606/232 |
| 5,258,016 | 11/1993 | DiPoto et al. | 606/232 |
| 5,318,577 | 6/1994 | Li | 606/232 |
| 5,326,205 | 7/1994 | Anspach, Jr. et al. | 606/232 |
| 5,358,511 | 10/1994 | Gatturna et al. | 606/232 |
| 5,423,860 | 6/1995 | Lizardi et al. | 606/232 |
| 5,505,735 | 4/1996 | Li | 606/232 |
| 5,520,696 | 5/1996 | Wenstrom, Jr. | 606/232 |
| 5,527,342 | 6/1996 | Pietrzak et al. | 606/232 |
| 5,545,180 | 8/1996 | Le et al. | 606/232 |
| 5,549,613 | 8/1996 | Goble et al. | 606/232 |
| 5,554,171 | 9/1996 | Gatturna et al. | 606/232 |
| 5,554,172 | 9/1996 | Horner et al. . | |
| 5,562,683 | 10/1996 | Chan . | |
| 5,562,687 | 10/1996 | Chan . | |
| 5,571,104 | 11/1996 | Li . | |
| 5,578,057 | 11/1996 | Wenstrom, Jr. . | |
| 5,584,860 | 12/1996 | Goble et al. . | |
| 5,626,613 | 5/1997 | Schmieding . | |
| 5,645,589 | 7/1997 | Li . | |
| 5,647,874 | 7/1997 | Hayhurst . | |
| 5,649,963 | 7/1997 | McDevitt . | |

*Primary Examiner*—Gary Jackson
*Attorney, Agent, or Firm*—Harness, Dickey & Pierce, P.L.C.

[57] ABSTRACT

A suture anchor system adapted for securing a suture to a bone. The suture anchor system includes a suture anchor which retains a portion of the suture within the bone. A driver handle having a first end and second end with a bore passing therethrough receives a portion of the suture anchor at the first end. A starter plunger having a first head and a first drive member is received at the second end of the driver handle. The starter plunger drives the suture anchor at least partially into the bone to a first depth. An insertion plunger having a second head and a second drive member is received at the second end of the driver handle. The insertion plunger drives the suture anchor fully into the bone to a second depth.

37 Claims, 5 Drawing Sheets

SUTURE ANCHOR SYSTEM

BACKGROUND OF THE INVENTION

1. Field of the Invention

This invention relates generally to an apparatus and method for use in orthopedic surgical procedures, and more particularly to a suture anchor system and method for securing soft tissues, tendons and ligaments to bone during orthopedic surgical procedures.

2. Discussion of the Related Art

It is often necessary to secure soft tissues, tendons and ligaments to bone during orthopedic surgical procedures in both human and animal patients. In the past, various devices and methods have been developed to accomplish this soft tissue attachment. In one known procedure, the orthopedic surgeon would make large incisions into the soft tissue to expose the bone, drill angled holes through the bone, and then thread the sutures through the holes in order to achieve ligament or soft tissue attachment. This known procedure was extremely complex and time consuming.

Due to the difficulties and potential complications associated with the previous procedures, alternate devices and methods have been developed. One such form of device for attaching soft tissues to a bone, developed to overcome some of the disadvantages of the previous devices and procedures, are suture anchors. A suture anchor generally comprises an anchor member which can be seated within the bone. A suture strand is secured to the anchor member and, thus, is available for assisting in the attachment of soft tissues, tendons and ligaments to the bone. Suture anchors generally require less complex and time consuming surgical procedures than those associated with earlier methods for attaching soft tissue to bone.

However, there are improvements which can be made to existing known suture anchors and the surgical procedures for securing the suture anchor and suture to the bone. It is, therefore, an object of the present invention to provide such a suture anchor system and method for securing soft tissues, tendons and ligaments to bone during orthopedic surgical procedures which improves upon existing devices and procedures.

SUMMARY OF THE INVENTION

In accordance with the teachings of the present invention, a suture anchor system and method for securing soft tissues, tendons and ligaments to bone during orthopedic surgical procedures is disclosed. This is basically achieved by using a two-step insertion procedure and driving instrument to impact the suture anchor at a first depth and a second depth.

In one preferred embodiment, a suture anchor system is used for securing a suture having a first end, a second end and a mid-portion therebetween to a bone. The suture anchor system includes a one-piece suture anchor having a rigid spear member with an impact tip and a tapered sidewall which is operable to pierce the bone. A plurality of wing members extend out from the spear member and are each separated by a longitudinal slot such that each wing member may be independently cantilevered. A suture retaining mechanism receives the suture and is defined by a bore laterally passing through a portion of the rigid spear member. An impact seat defined by the inner sidewalls of the wing members and an impact base is engaged by a driving instrument along an axial centerline of the suture anchor such that upon engagement by the driving instrument, the suture anchor is operable to be impacted into the bone.

In another preferred embodiment, the suture anchor system includes a suture anchor which retains a portion of the suture within the bone. A driver handle having a first end and a second end with a bore passing therethrough for receiving a portion of the suture anchor. A starter plunger having a first head and a first drive member is received by the second end of the bore such that the starter plunger drives the suture anchor at least partially into the bone to a first depth. An insertion plunger having a second head and a second drive member is received by the second end of the bore such that the insertion plunger drives the suture anchor fully into the bone to a second depth.

In another preferred embodiment, the suture anchor system includes a suture anchor which retains a portion of the suture within the bone. A driving instrument drives the suture anchor into the bone. A resilient retaining member slidably retains the suture relative to the driving instrument such that the suture may be slidably removed axially from the driving instrument.

In another preferred embodiment, a method for securing a suture to a bone using a suture anchor includes the steps of positioning a first portion of the suture anchor within a driving instrument with a second portion extending out from the driving instrument. At least the second portion of the suture anchor is driven into the bone to a first depth such that the first portion of the suture anchor substantially remains within the driving instrument. The first and second portions of the suture anchor are then fully driven into the bone to a second depth.

In another preferred embodiment, the suture anchor system includes a suture anchor operable to retain a portion of the suture within the bone. A driving instrument having a depth control mechanism is used to drive the suture anchor to a first depth within the bone and to a second depth within the bone. A first portion of the suture anchor is driven to the first depth and the first portion and a second portion of the suture anchor are driven to the second depth.

Use of the present invention provides a suture anchor system and a method for securing soft tissues, tendons and ligaments to bone during orthopedic surgical procedures. As a result, the disadvantages associated with the currently available suture anchors have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENT(S)

The following description of the preferred embodiments concerning a suture anchor system and method for securing soft tissues, tendons and ligaments to bone during orthopedic surgical procedures is merely exemplary in nature and is not intended to limit the invention or its application or uses. Moreover, while the present invention is described in detail below with reference to performing the surgical procedure on a human patient, it will be appreciated by those skilled in the art that the present invention is clearly not limited to merely human patients and may also be used on animal patients as well. It should further be noted that any specific dimensions discussed herein are merely exemplary in nature and may vary depending on the patients' size and needs.

Referring to FIGS. 1–4, an impact-type self-driving suture anchor 10 according to the teachings of the first preferred embodiment in the present invention is shown. The suture anchor 10 is preferably constructed from 316L stainless steel or other suitable biocompatible material such as titanium alloy, cobalt chrome, ceramic, resorbable materials, etc. The suture anchor 10 is used for attaching soft tissues, tendons and ligaments to bone during orthopedic surgical repairs to both human and animal patients. It should further be understood that the suture anchor 10 may also be used with other types of surgical procedures as well. The suture anchor 10 is formed from a single piece of material that is machined into the shape shown in FIGS. 1–4 without the need for a multi-piece construction thereby reducing the overall material and manufacturing costs for the suture anchor 10.

To provide a means for piercing the cortex of the bone and securely engage the bone, the suture anchor 10 includes a rigid or substantially solid conical spear member 12. The spear member 12 includes an impact point or tip 13 and a cone shaped outer sidewall 14 which are used for piercing the bone to which the soft tissue is to be subsequently secured. To provide a means for retaining the suture anchor 10 within the bone, the suture anchor 10 further includes four (4) separate flange or wing members 16 which extend rearwardly from the spear member 12. The wing members 16 are separated from one another by four (4) longitudinally extending slots 18 which allows for independent movement of each wing member 16. Each of the wing members 16 angles generally outward from the central longitudinal axis or spear member 12 of the suture anchor 10 at an angle, identified by reference numeral 20, while the cone shaped sidewall 14 of the spear member 12 angles outward relative to the longitudinal axis of the suture anchor 10 at an angle, identified by reference numeral 22. The angle 22 will generally always be larger than the angle 20 with a transition point 23 occurring therebetween. Such a transition creates a smaller hole within the bone versus a suture anchor that does not include a transition point.

The wing members 16 define an internal truncated conical cavity or impact seat 24 defined by inner angled sidewalls 26 and a planer impact base 28. The planer impact base 28 has a substantially circular periphery 30. Passing laterally through the spear member 12 is a suture retaining means or a suture hole 32 which is aligned adjacent to a pair of opposed longitudinal extending slots 18. The slots 18 have a width that is generally greater than or equal to the diameter of the suture hole 32. A pair of polished slots or notches 34 are also formed adjacent to the hole 32 and are axially aligned with the slots 18 to provide for clearance of one or more sutures passing through the hole 32 such that the sutures do not extend substantially beyond the outer periphery 36 of the suture anchor 10. Here again, the polished slots 34 have a width that is also greater than or equal to the diameter of the suture hole 32. The suture anchor 10 may be sized to receive various sized sutures, such as a #5 or #2 suture.

Turning to FIGS. 5–9, a driving instrument 40 is shown which provides a means for driving the suture anchor 10 into the bone. The driving instrument 40 includes a driver handle 42, a starter plunger 44 and an insertion plunger 46. The driver handle 42, the starter plunger 44 and the insertion plunger 46 are each preferably constructed from 17-4PH stainless steel or other suitable material. The driving instrument 40 is operable to enable the suture anchor 10 to be impacted or driven through and into the bone to secure the suture anchor 10, as well as a suture, within the bone without the need for preparing a pilot hole in the bone. However, the driving instrument 40 may also be used with a pilot hole should this option be desired.

Figures 1, 2, 3, 4, 5, 6, 7, 8:
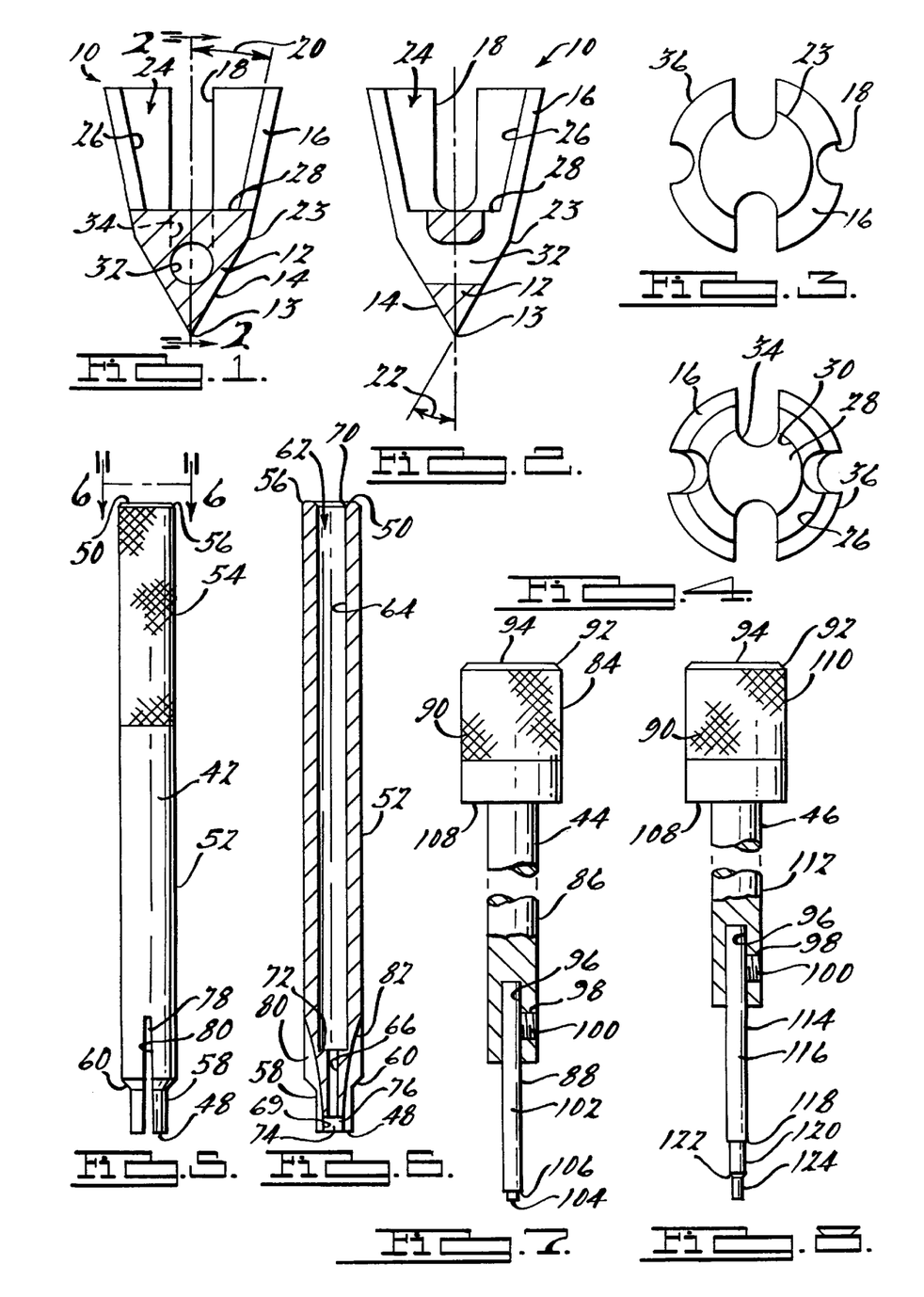
FIG. 1 is a side cross-sectional view of a suture anchor according to the teachings of a first preferred embodiment of the present invention.
FIG. 2 is a side cross-sectional view of the suture anchor shown in FIG. 1 rotated 90° relative to axis 2—2 of FIG. 1.
FIG. 3 is a front elevational view of the suture anchor shown in FIG. 1.
FIG. 4 is a rear elevational view of the suture anchor shown in FIG. 1.
FIG. 5 is a side elevational view of a driver handle according to the teachings of the first preferred embodiment of the present invention.
FIG. 6 is a side cross-sectional view of the driver handle shown in FIG. 5, taken along line 6—6 of FIG. 5.
FIG. 7 is a side partial cross-sectional view of a starter plunger according to the teachings of the first preferred embodiment of the present invention.
FIG. 8 is a side partial cross-sectional view of an insertion plunger according to the teachings of the first preferred embodiment of the present invention.

The driver handle 42 includes a first distal end 48 and a second proximal end 50. The driver handle 42 includes an elongated cylindrical body 52 having a diamond knurled surface 54 at the second proximal end 50 and a chamfer 56. Concentric with the cylindrical body 52 is a cylindrical positioning seat 58 which extends from a conically tapered portion 60. The driver handle 42 further includes a longitudinal axially extending bore 62 passing through the driver handle 42. The axial bore 62 is defined by a first cylindrical sidewall 64, a second cylindrical sidewall 66 and a third cylindrical sidewall 68. In general, the first cylindrical sidewall 64 has a larger diameter then the third cylindrical sidewall 68 and the third cylindrical sidewall 68 has larger diameter than the second cylindrical sidewall 66. The cylindrical sidewall 64 includes a tapered countersink 70 and a stepped shoulder 72. The cylindrical sidewall 68 defines a counterbore cavity 74 having a annular planer base 76. The counterbore cavity 74 is used to nestingly receive and seat the wing portion of the suture anchor 10.

A slot or pair of grooves 78 pass through the centerline of the driver handle 42 at the first distal end 48. The slot 78 passes entirely through the distal end 48 of the driver handle 42 through the counterbore cavity 74. The slot 78 continues to run along the positioning seat 58, the tapered portion 60, and the cylindrical body 52. In this region, each side of the slot or groove 78 is defined by the straight sidewalls 80 and an arcuate sidewall 82. The slot or grooves 78 provide for clearance of the sutures used to pass through the suture anchor 10, thereby enabling the sutures to not extend substantially beyond the outer periphery of the driver handle 42 at the distal end 48. Here again, the driving instrument 40, including the driver handle 42, may be sized for any size suture desired.

Turning now to FIG. 7, the starter plunger 44 which is slidably received within the second end 50 of the driver handle 42 includes an impact head 84, an elongated cylindrical drive shaft 86 and a removable plunger pin 88. The impact head 84 includes a diamond knurled surface 90. The diamond knurled surface 90 provides a grippable surface contour to enable easy insertion and removal of the starter plunger 44 from within the driver handle 42. The impact head 84 further includes a chamfer 92 and a labeled top surface 94 having an engraved "S" therein for identifying the plunger as the starter plunger 44. The impact head 84 may be a separate head which is affixed to the cylindrical drive shaft 86 or an integral head.

The drive shaft 86 includes a bore 96 which is operable to receive a portion of the removable plunger pin 88. The plunger pin 88 is secured within the bore 96 by use of a threaded set screw 98 passing through a laterally extending threaded bore 100. The bore 96 along with the threaded set screw 98 enables the plunger pin 88 to be replaced should the plunger pin 88 be damaged or if a different length plunger pin 88 is desired to provide adjustable depth control of the suture anchor 10. It should also be noted that the plunger pin 88 in the starter plunger 44, as well as in the insertion plunger 46 is preferably formed from a different type stainless steel as compared to the driver handle 42. In this way, galling between the components is reduced as the plunger pin 88 rides within the second cylindrical sidewall 66.

The plunger pin 88 extends out from the drive shaft 86 and includes a first cylindrical sidewall 102 and a second smaller cylindrical sidewall 104. The first cylindrical sidewall 102 has a diameter of about 0.093 inches and the second cylindrical sidewall 104 has a diameter of about 0.063 inches. The second cylindrical sidewall 104 having the smaller diameter enables the plunger pin 88 to sit fully and directly atop the circular impact base 28 of the suture anchor 10 which has a slightly larger diameter. The first cylindrical sidewall 102 having the larger diameter increases the overall strength of the plunger pin 88 by about 300% versus utilizing the smaller diameter throughout the length of the plunger pin 88, thereby providing substantial resistance to bending of the plunger pin 88. The transition between the first cylindrical sidewall 102 and the second cylindrical sidewall 104 is a shoulder 106.

The cylindrical drive shaft 86 is slidably received within the first cylindrical sidewall 64 of the driver handle 42 and the plunger pin 88 is slidably received within both the cylindrical sidewall 66 and the counterbore cavity 74 of the driver handle 42. With the impact ledge 108 sitting atop the proximal end 50 of the driver handle 42, and the suture anchor 10 positioned partially within the counterbore 74, the wing members 16 of the suture anchor 10 are positioned slightly away from the annular base 76 of the counterbore cavity 74 (see FIG. 10B), this enables the entire driving force to be applied along the axial centerline of the suture anchor 10 into the rigid or substantially solid portion of the spear member 12 or impact base 28. This further reduces the possibility of damaging the suture anchor 10, as well as provides a straight line driving of the suture anchor 10 into the bone for stable driving. Such stability reduces the chance that the suture anchor 10 will be impacted on an angle or tumble as it is being impacted or driven into the bone.

Referring now to FIG. 8, the insertion plunger 46 is shown also having an impact head 110, a driving shaft 112 and a removable plunger pin 114. The impact head 110 and the driving shaft 112 is substantially the same as the impact head 84 and the driving shaft 86 of the starter plunger 44 except that the top 94 of the impact head 110 includes an engraved label "I" identifying the plunger to be the insertion plunger 46. The plunger pin 114 includes a first cylindrical sidewall 116, a first shoulder 118, a second smaller cylindrical sidewall 120, a second tapered shoulder 122 and a third smaller cylindrical sidewall 124.

Figures 9, 10A, 10B, 10C:
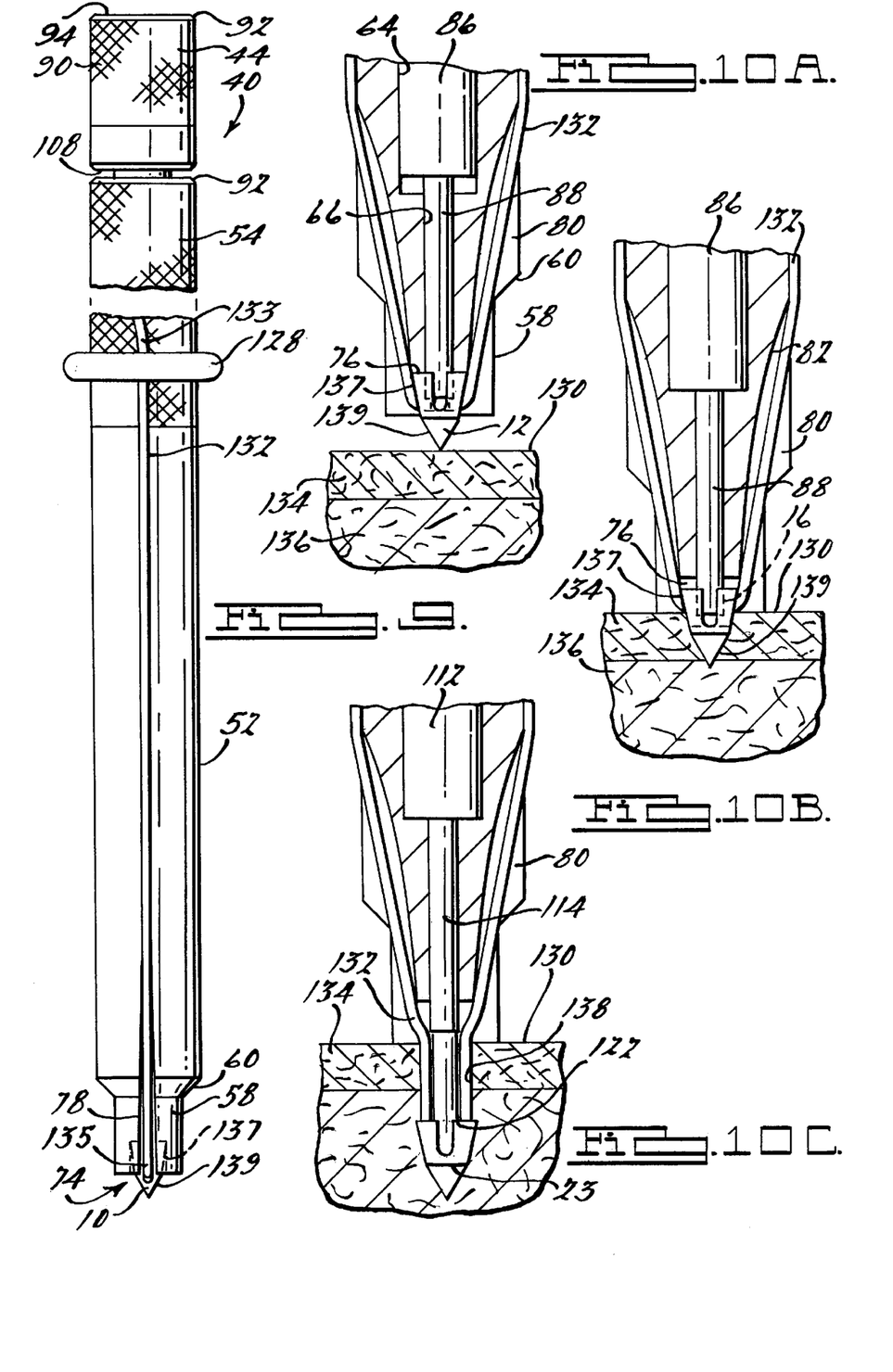
FIG. 9 is an assembled side elevational view of the suture anchor system according to the teachings of the first preferred embodiment of the present invention shown using the starter plunger.
FIGS. 10A–10D illustrates a method for securing the suture anchor and a suture to a bone according to the teachings of the first preferred embodiment of the present invention.

With the insertion plunger 46 fully inserted within the driver handle 42, the second and third cylindrical sidewalls 120 and 124, respectfully, only extend out beyond the distal end 48 of the driver handle 42, as shown in FIG. 10C. The length of the third cylindrical sidewall 124 is sized such that upon engagement with the impact base 28 of the suture anchor 10, the ends or tops of the wing members 16 are aligned adjacent to the shoulder 122, thereby enabling full cantilevered movement of the wing members 16 adjacent to the third cylindrical sidewall 124. The diameter of the third cylindrical sidewall 124 is also sized to fully engage the planer impact base 28 and provide clearance for the thickness of the wing members 16 as they move. The diameter of the second cylindrical sidewall 120 is sized such that it is smaller than the diameter of the circular base 28 so that when the second cylindrical sidewall 120 passes through the hole impacted within the bone, the plunger pin 114 does not engage or get stuck within this hole. The ledge 108 is also used for depth control as the ledge 108 sits atop the proximal end 50 of the driver handle 42. The ledge 108 also provides a visual guide as to how far the suture anchor 10 needs to be impacted into the bone.

The method of securing the suture anchor 10, will now be described utilizing the driving instrument 40 with reference to FIGS. 10A–10C. Initially, the size of the suture to be used to secure the soft tissue to the bone 130 is determined. The size of the suture anchor 10, as well as the driving instrument 40 will vary depending on which size suture is used. Once a suture size is selected, a length of suture 132 having two (2) ends 133 and a mid-portion 135 is passed through the suture hole 32 and positioned along notches 34 and aligned with the longitudinal slots 18. A first portion 137 of the suture anchor 10 is then positioned, wing members 16 first, within the counterbore cavity 74 of the driver handle 42. The suture 132 extends up along and through the grooves 78 adjacent to the sidewall 82 and a second portion 139 of the suture anchor 10 extends out of the counterbore cavity 74.

At least one resilient O-ring 128 is then slidably engaged from the distal end 48 of the driver handle 42 up along the cylindrical body 52 and on to the knurled surface 54, axially capturing the two ends 133 of the suture 132 between the resilient O-ring 128 and the knurled surface 54. The knurled surface 54 provides for better or enhanced attachment of the resilient O-ring 128 to the driver handle 42, as well as more surface area to capture and slidably retain the suture 132 against the driver handle 42. The suture 132 along with the O-ring 128 slidably retains the first portion 137 of the suture anchor 10 in place within the counterbore cavity 74.

The drive shaft 86 and plunger pin 88 are then slidably received within the bore 62 passing through the driver handle 42 until the impact ledge 108 is positioned adjacent to the proximal end 50 of the driver handle 42. The spear member 12 of the suture anchor 10 is then positioned against the bone 130, as shown in FIG. 10A, in an area where it is desired to secure a soft tissue ligament or within a predrilled pilot hole having a diameter smaller than the transition point 23. With the suture anchor 10 positioned against the bone 130, the first portion 137 of the suture anchor 10 will sit fully within the counterbore cavity 74 such that the wing members 16 are engaged against the annular base 76 of the counterbore cavity 74 and the second portion 139 extends therefrom. This positioning of the suture anchor 10 within the counterbore cavity 74 prevents the suture anchor 10 from tumbling when impacted.

With the suture anchor 10 properly positioned and centrally stabilized by the plunger pin 88 of the starter plunger 44, the impact head 84 of the starter plunger 44 is struck with a suitable mallet such that only the plunger pin 88 and not the annular base 76 applies a force through the axial centerline of the suture anchor 10. This impacts only the second portion 139 or about thirty percent (30%) to fifty percent (50%) of the suture anchor 10 within the cortical region 134 of the bone 130 up to a first depth controlled by ledge 108 and distal end 48, while also compressing the wing members 16. By using only the plunger pin 88 to drive the suture anchor 10 along the axial centerline, the wing members 16 are not engaged by the annular base 76 of the counterbore 74, thereby reducing the potential for damage to the wing members 16. Moreover by only impacting or driving the second portion 139 (i.e. 30%–50%) of the suture anchor 10 up to a first depth within the cortex 134, at least about 50% of the suture anchor 10 or the first portion 137 is still within the counterbore cavity 74. This also insures driving stability so that the suture anchor 10 will not be driven on an angle or tumble while it is being driven into the cortex 134, which may occur if the suture anchor 10 is initially fully driven into the bone 130 with only the insertion plunger 46 or without the aid of the counterbore cavity 74.

With the suture anchor 10 partially engaged within the cortex 134 of the bone 130, the starter plunger 44 is slidably removed from the driver handle 42 and the insertion plunger 46 is then slidably received within the second end 50 of the driver handle 42. With the plunger pin 114 engaging the suture anchor 10, and the distal end 48 of the driver handle 42 held firmly against the bone 130, the suture anchor 10 is fully driven into the cancellous portion 136 of bone 130 to a second depth, as shown in FIG. 10C using the ledge 108 for both visual and mechanical depth control. The hole 138 created through the cortex 134 of the bone 130 generally has a diameter slightly smaller than the largest rigid portion of the suture anchor 10 which is about the diameter at the transition point 23. Once the suture anchor 10 passes through the cortical portion 134 of the bone 130, and is fully seated within the cancellous portion 136, the wing members 16 anchor the suture 132 within the bone 130. The driving instrument 40 is then removed by simply pulling the driver handle 42 upwards enabling the suture 132 to be slidably and axially removed from the O-ring 128. Once removed, the two ends 133 of the suture 132 are firmly pulled to further secure the suture anchor 10 within the cancellous portion 136 and also forces bone within the cavity 24 of the suture anchor 10 providing further securement. A soft tissue and/or ligament is then secured adjacent to the bone surface with the suture 132 using known techniques such as during collateral ligament reconstructive or re-attachment surgery.

The second preferred embodiment of the present invention will now be described with reference to FIGS. 11–12B. In this regard, like reference numerals will be used to identify similar structures as described with respect to the first preferred embodiment of the present invention. A solid driving instrument 140 is shown which is used for driving and securing the suture anchor 10 within the bone 130. The driving instrument 140 includes an elongated cylindrical body 142 having a knurled surface 144 and an impact head 146 at its proximal end 148. At the distal end 150 there is a cylindrical drive shaft 152 which extends from a conically tapered portion 154. The drive shaft 152 includes a truncated conical shaped finger 156 which is used to nestingly receive the cavity or impact seat 24 of the suture anchor 10. The driving instrument 140 further includes a pair of opposed grooves or slots 158 which are operable to receive the suture 132 such that the suture substantially does not extend out beyond the outer periphery of the driving instrument 140. The suture 132 is again secured or held adjacent to the cylindrical body 142 by means of the resilient O-ring 128 along the knurled surface 144.

Figures 10D, 11, 12A, 12B, 13, 14, 15A, 15B:
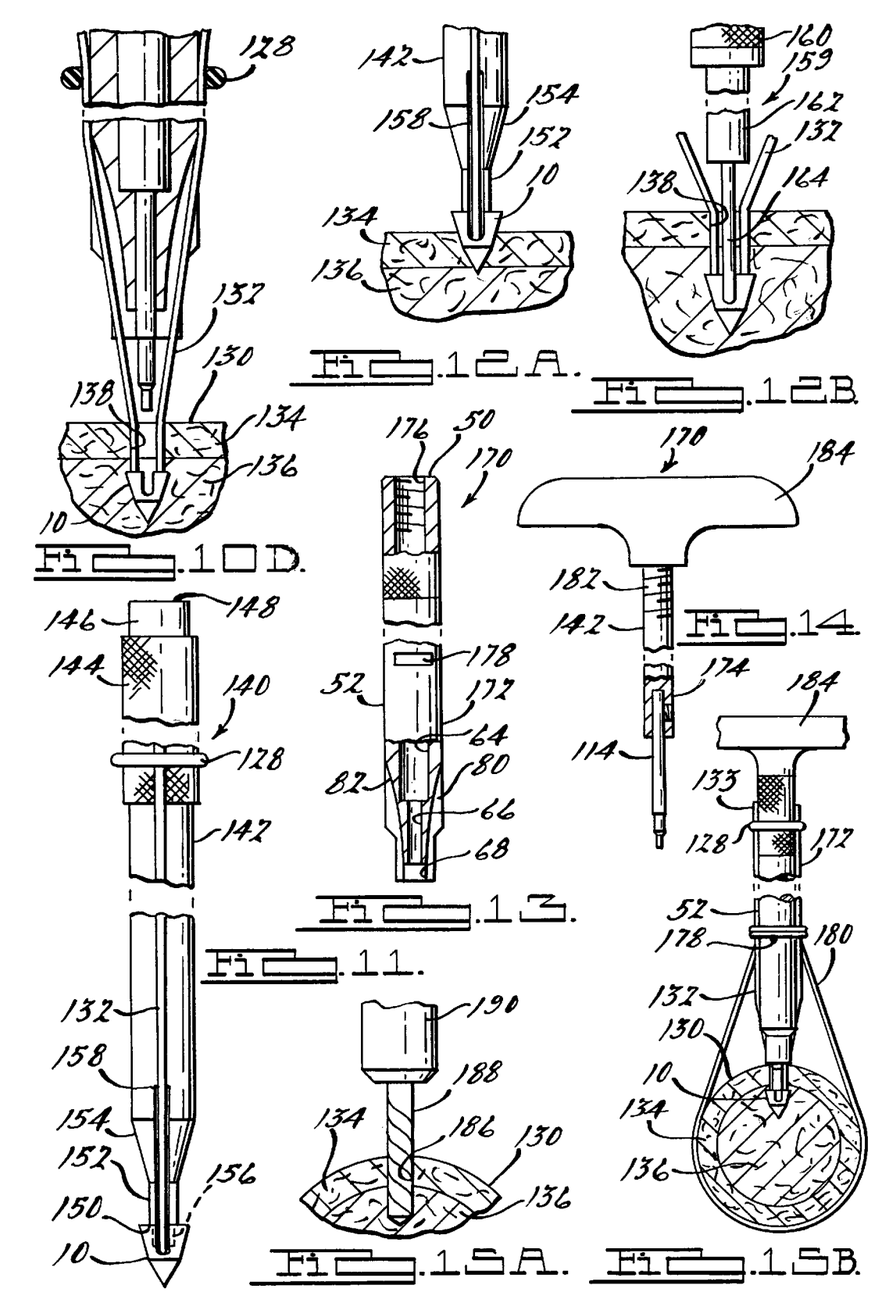
FIG. 11 is a side elevational view of a suture anchor system according to the teachings of a second preferred embodiment of the present invention.
FIGS. 12A–12B illustrates a method for securing the suture anchor and a suture to a bone according to the teachings of the second preferred embodiment of the present invention.
FIG. 13 is a side partial cross-sectional view of a threaded driver handle according to the teachings of a third preferred embodiment of the present invention.
FIG. 14 is a side partial cross-sectional view of a threaded insertion plunger according to the teachings of the third preferred embodiment of the present invention.
FIGS. 15A–15B illustrates a method for securing the suture anchor and a suture to a bone according to the teachings of the third preferred embodiment of the present invention.

With the suture anchor 10 positioned against the bone 130, the suture anchor 10 is first driven into the cortex 134 of the bone 130 adjacent to, but not past, the depth control of the cylindrical drive shaft 152, as shown in FIG. 12A, so that the suture anchor 10 just pierces the cortex 134 to a first depth. It should be noted that since the finger 156 is conically shaped to substantially conform to the cavity 24, the wing members 16 are not able to substantially cantilever inward upon insertion into the cortex 134, thereby creating a larger hole 138 within the bone 130. Once the suture anchor 10 penetrates the cortex 134, the driving instrument 140 is removed by simply pulling the driving instrument 140 away from the suture anchor 10, thereby slidably removing the suture 132 from under the resilient O-ring 128.

A punch 159 having a shape somewhat similar to the starter plunger 44 is then used to fully drive the suture anchor 10 into the cancellous portion 136 of the bone 130 to securely anchor the suture anchor 10 within the bone 130. The punch 159 includes an impact head 160, a drive shaft 162 and a plunger pin 164 having a similar shape as the plunger pin 88 in the starter plunger 44. The diameter of the drive shaft 162 is sized such that it prevents the drive shaft 162 from passing within the hole 138, thereby providing a mechanism to control the second depth of insertion of the suture anchor 10. Once the punch 159 is removed, the two ends of the suture 132 are again pulled tautly to insure that the anchor 10 is fully secured within the cancellous portion 136 of the bone 130.

A third preferred embodiment of the present invention will now be described with reference to FIGS. 13–15B. In this regard, like reference numerals will be used to identify similar structures as described with respect to the other preferred embodiments of the present invention. A driving instrument 170 is shown including a driver handle 172 and an insertion plunger 174. The driver handle 172 is substantially similar to the driver handle 42 except for including a threaded sidewall 176 at the proximal end 50 of the driver handle 172 and a pair of opposed grooves 178 formed along the outer cylindrical body 52 which are used to receive a securement wire 180, further discussed herein. The insertion plunger 174 is substantially the same as the insertion plunger 46 except that it includes an outer threaded cylindrical portion 182 and a "T"-shaped handle or head 184.

The method for securing the suture anchor 10 utilizing the driving instrument 170 first includes the step of either drilling a pilot hole 186 through the cortex 134 utilizing a drill 188 and a driver 190. Alternatively, the starter plunger 44 may be used to impact and drive the suture anchor 10 through the cortex 134 to a first depth. Once the pilot hole 186 is drilled or the suture anchor 10 driven into the cortex 134, the driving instrument 170 is secured to the bone 130 by means of the securement wire 180 which is wrapped about the bone 130, through the grooves 178 and secured to the cylindrical body 52. This insures that the driving instrument 170 does not pull away from the bone 130 as the suture anchor 10 is threadably driven into the bone 130. With the driver handle 172 firmly secured, the T-handle or head 184 of the insertion plunger 174 is rotated such that the threaded portion 182 threadably engages the inner threaded bore 176 to threadably drive the suture anchor 10 through the cortex 134 and into the cancellous portion 136 of the bone 130 to a second depth as the plunger pin 114 engages the impact base 28. Once the insertion plunger 174 is fully threadably seated within the driver handle 172, the securement wire 180 is removed from about the bone 130 and the driving instrument 170 is simply pulled away from the suture anchor 10 leaving behind the two ends 133 of the suture 132 for use and securement of a soft ligament tissue adjacent to the bone 130.

A fourth preferred embodiment in the present invention will now be described with reference to FIGS. 16A–16B. In this regard, like reference numerals will be used to identify similar structures as described with respect to the other preferred embodiments of the present invention. An assembled driving instrument 192 is shown including a driver handle 194 and a starter/insertion plunger 196. The driver handle 194 is substantially similar to the driver handle 42 except that it includes a larger diameter knurled portion 198 that arcuately tapers along taper 200 to the cylindrical body 52. The knurled portion 198 is enlarged to accommodate an axially extending slot or groove 202 that passes partially along one side of the driver handle 194.

The starter/insertion plunger 196 is substantially similar to the insertion plunger 46 except that it further includes a laterally extending post 204 which is removably received within a bore 205 of the driving shaft 112 via a set screw or other appropriate securing mechanism. The post 204 is used to control the first and second insertion depths of the suture anchor within the bone 130, thereby eliminating the need for use of a separate starter plunger 44 and a separate insertion plunger 46. In other words, the depth control post 204 is positioned at the appropriate distance away from the impact ledge 108 of impact head 110 so that the starter/insertion plunger 196 may be used for both the initial impacting to a first depth and full impacting of the suture anchor 10 to a second depth within the bone 130.

Specifically, with the first portion 137 of the suture anchor 10 positioned within the counterbore cavity 74 and the second portion 139 of the suture anchor 10 extending out from the distal end 48 of the driver handle 194, the starter/insertion plunger 196 is axially rotated such that the depth control post 204 is not aligned with the groove 202. The head 110 of the starter/insertion plunger 196 is impacted with an appropriate mallet until the depth control post 204 comes to rest along the proximal end 50 of the driver handle 194, as shown in FIG. 16A. With the post 204 positioned against the proximal end 50, the second portion 139 of the suture anchor 10 is impacted through the cortex 134 of the bone 130 to a first depth with the first portion 137 still remaining axially aligned within the counterbore cavity 74. This prevents the suture anchor 10 from tumbling or being impacted through the bone 130 on an angle.

Figures 16A, 16B:
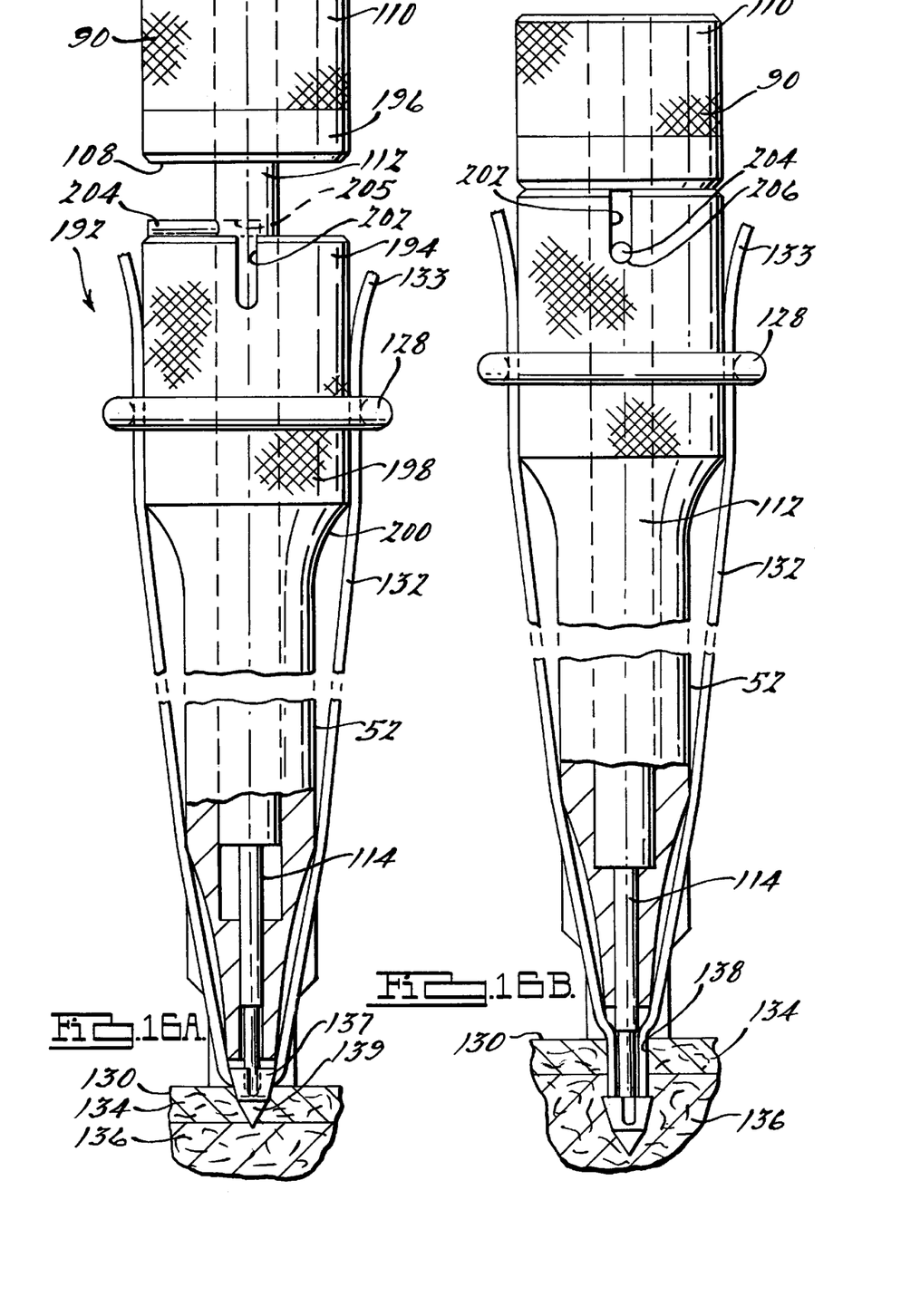
FIGS. 16A–16B are assembled side partial cross-sectional views of the suture anchor system according to the teachings of a fourth preferred embodiment of the present invention.

Once the suture anchor 10 is partially impacted into the bone 130 up to the first depth, the starter/insertion plunger 196 is then rotated such that the depth control pin 204 is in alignment with the groove 202, as shown in FIG. 16B. The post 204 is sized such that it has a diameter which is slightly smaller than the width of the groove 202 so that the post 204 is nestingly received within the groove 202. With the post 204 in alignment with groove 202, the head 110 is again impacted to fully drive the suture anchor 10 within the cancellous portion 136 of the bone 130. The suture anchor 10 is fully impacted into the bone 130 up to a second depth upon the post 204 seating within the bottom 206 of the U-shaped slot 202. The driving instrument 192 provides for the two step insertion procedure while eliminating one of the separate plungers, via the use of the depth control post 204. Further depth control may also be achieved by providing multiple laterally extending bores 205 through the drive shaft 112 and appropriately positioning the post 204 therein.

A fifth preferred embodiment of the present invention will now be described with reference to FIGS. 17A–17B. In this regard, like reference numerals will again be used to identify similar structures as described with respect to the other preferred embodiments of the present invention. An assembled driving instrument 210 is shown including a driver handle 212 and a starter/insertion plunger 214. The driver handle 212 is substantially similar to the driver handle 194 except that it includes a laterally milled slot 216, passing through the cylindrical body 52 of the driver handle 212. The starter/insertion plunger 214 is substantially similar to the starter/insertion plunger 196 except that it includes a stepped shoulder 218 and a laterally extending depth control key 220 which is formed by milling opposed lateral sides of key 220. Depth control key 220 is sized such that it is operable to be fully nestingly received within the slot 216.

Figure 17A:
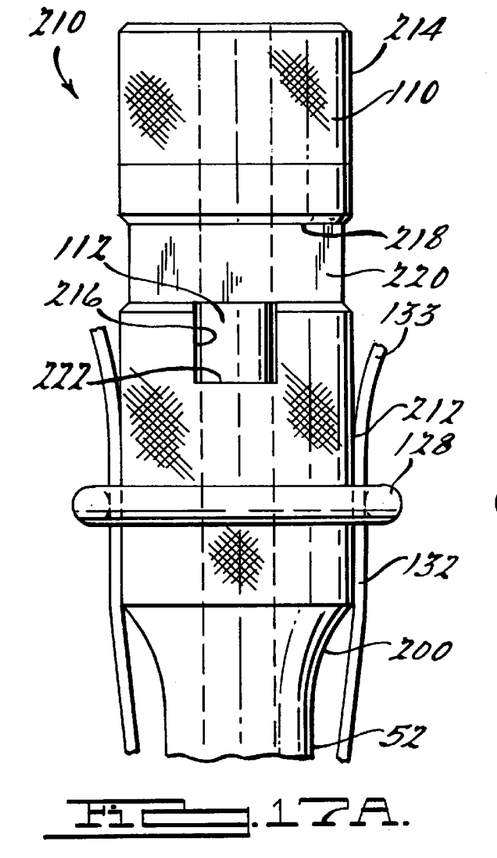
FIGS. 17A–17B are assembled side partial views of the suture anchor system according to the teachings of a fifth preferred embodiment of the present invention.
Figure 17B:
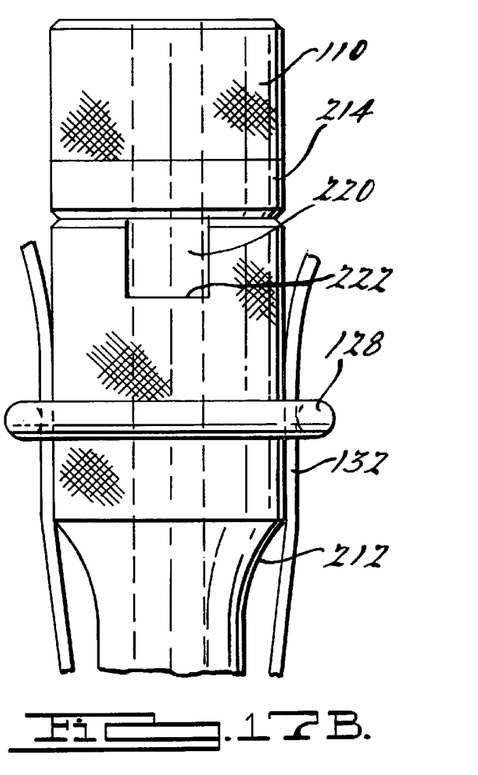

The operation of the driving instrument 210 is similar to the driving instrument 192 in that the depth control key 220 is first rotated out of alignment with the slot 216 such that when the head 110 of the starter/insertion plunger 214 is impacted, the depth control key 220 comes to rest atop the proximal end 50 of the driver handle 212, as shown in FIG. 17A. With the depth control key 220 positioned atop the proximal end 50, the second portion 139 of the suture anchor 10 is impacted through the cortex 134 of the bone 130 to a first depth with the first portion 137 still remaining axially aligned within the counterbore cavity 74. Once the suture anchor 10 is partially impacted into the bone 130 up to the first depth, the starter/insertion plunger 214 is then rotated such that the depth control key 220 is in alignment with the slot 216, as shown in FIG. 17B. With the depth control key 220 in alignment with the slot 216, the head 110 is again impacted to fully drive the suture anchor 10 within the cancellous portion 136 of the bone 130. The suture anchor 10 is thus fully impacted into the bone 130 up to a second depth upon the depth control key 220 fully seating within the bottom 222 of the slot 216. One benefit to this embodiment is that the sheer force is extended fully laterally across two sides of the driver handle 212 in contrast to the fourth preferred embodiment in which the depth control post 204 is only engaged on one side of the driver handle 194.

It should further be noted that various other embodiments may also be implemented to achieve this two-step insertion process providing controlled insertion to a first depth and subsequently to a second depth, thereby preventing the suture anchor 10 from tumbling or being impacted through the bone 130 on an angle. For example, the post 204 could be spring-biased such that it first engages the proximal end 50 of the driver handle 194 with the post 204 being extended laterally from the drive shaft 112. The post 204 may then be laterally received within the bore 205, via a spring bias mechanism, thereby eliminating the need for the groove 202. Alternatively, the post 204 can pass fully through the shaft 112 thereby dispersing the sheer stress along both sides of the driver handle 194 similar to the driving instrument 210.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A suture anchor system for securing a suture having a first end, a second end and a mid-portion there between to a bone, said suture anchor system comprising:

a one-piece suture anchor having,
      a rigid spear member having an impact tip and a tapered sidewall, said rigid spear member operable to pierce the bone;
      a plurality of wing members extending out from said rigid spear member, each wing member separated by a longitudinal slot whereby each wing member may independently cantilever;
      a suture retaining bore passing through a portion of said rigid spear member, said suture retaining bore operable to receive the mid-portion of the suture; and
      a truncated conical impact seat defined by inner sidewalls of said wing members and an impact base, said impact base operable to be firmly engaged by a driving instrument along an axial centerline of said suture anchor, said driving instrument including a solid drive member having a truncated conical shape which is nestingly received by said impact seat, wherein upon engagement by said driving instrument, said suture anchor is operable to be impacted into the bone.

2. The suture anchor system as defined in claim 1 wherein said driving instrument includes a driver handle, a starter plunger and an insertion plunger.

3. A suture anchor system for securing a suture having a first end, a second end and a mid-portion there between to a bone, said suture anchor system comprising:

a one-piece suture anchor having,
      a rigid spear member having an impact tip and a tapered sidewall, said rigid spear member operable to pierce the bone;
      a plurality of wing members extending out from said rigid spear member, each wing member separated by a longitudinal slot whereby each wing member may independently cantilever;
      a suture retaining bore passing through a portion of said rigid spear member, said suture retaining bore operable to receive the mid-portion of the suture; and
      a truncated conical impact seat defined by inner sidewalls of said wing members and an impact base, said impact base operable to be firmly engaged by a driving instrument along an axial centerline of said suture anchor, said driving instrument includes a driver handle having a first end and a second end with a bore passing therethrough, said first end including a counterbore seat operable to receive a portion of said suture anchor, wherein upon engagement by said driving instrument, said suture anchor is operable to be impacted into the bone.

4. The suture anchor system as defined in claim 3 wherein said driving instrument further includes a starter plunger having a head and a drive member, said second end of said bore operable to receive said drive member, whereby said starter plunger is operable to drive said suture anchor at least partially into the bone upon engagement of said drive member with said impact base.

5. The suture anchor system as defined in claim 3 wherein said driving instrument further includes an insertion plunger having a head and a drive member, said second end of said bore operable to receive said drive member, whereby said insertion plunger is operable to drive said suture anchor fully into the bone upon engagement of said drive member with said impact base.

6. The suture anchor system as defined in claim 5 wherein said second end of said bore includes a first threaded portion and said drive member includes a second threaded portion, wherein said first and second threaded portions threadably engage one another to threadably drive said suture anchor fully into the bone.

7. The suture anchor system as defined in claim 1 further comprising a resilient retaining member operable to slidably axially retain the suture adjacent to the driving instrument.

8. The suture anchor system as defined in claim 3 wherein said driving instrument further includes a starter/insertion plunger having a head and a drive member, said second end of said bore operable to receive said drive member, said drive member further including a depth control member operable to be received within a slot in said driver handle, whereby said starter/insertion plunger is operable to drive said suture anchor partially into the bone to a first depth with the depth control member engaging said first end of said drive handle and operable to drive said suture anchor fully into the bone to a second depth upon engagement of the depth control member within said slot of said driver handle.

9. The suture anchor system as defined in claim 1 wherein said conically shaped sidewall of said spear member angles at a first angle relative to an axial centerline of said suture anchor and said wing members angle at a second angle relative to said axial centerline, said first angle being larger than said second angle.

10. A suture anchor system for securing a suture to a bone, said suture anchor system comprising:

a suture anchor operable to retain a portion of the suture within the bone;
    a driver handle having a first end and a second end with a bore passing therethrough, said first end operable to receive a portion of said suture anchor;
    a starter plunger having a first head and a first drive member, said second end with said bore operable to receive said first drive member, said starter plunger operable to drive said suture anchor at least partially into the bone to a first depth; and
    an insertion plunger having a second head and a second drive member, said second end with said bore operable to receive said second drive member, said insertion plunger operable to drive said suture anchor fully into the bone to a second depth, at least one of said first drive member and said second drive member including a drive shaft and a plunger pin removably received by said drive shaft.

11. The suture anchor system as defined in claim 10 wherein said first end of said driver handle defines an annular counterbore seat which is operable to nestingly receive a portion of said suture anchor.

12. The suture anchor system as defined in claim 10 wherein said plunger pin includes a first cylindrical sidewall having a first diameter and a second cylindrical sidewall having a second diameter, wherein said second cylindrical sidewall having said second diameter is operable to fully engage said suture anchor along an axial centerline of said suture anchor.

13. The suture anchor system as defined in claim 10 wherein said plunger pin includes a first cylindrical sidewall having a first diameter, a second cylindrical sidewall having a second diameter, and a third cylindrical sidewall having a third diameter, wherein said third cylindrical sidewall having said third diameter is operable to fully engage said suture anchor along an axial centerline of said suture anchor and said second cylindrical sidewall having said second diameter is operable to be inserted into a hole created by said suture anchor without substantially engaging said hole.

14. The suture anchor system as defined in claim 10 further comprising a resilient O-ring operable to be engaged about said driver handle to slidably axially retain the suture adjacent to said driver handle while retaining said suture anchor within said first end of said bore.

15. The suture anchor system as defined in claim 10 wherein said first head and said second head each control the depth of said first drive member and said second drive member, respectively, thereby controlling the depth said suture anchor is driven into the bone.

16. The suture anchor system as defined in claim 10 wherein said first end of said bore of said driver handle is threaded and a portion of said second drive member of said insertion plunger is threaded, wherein upon rotating said second head of said insertion plunger, said insertion plunger is threadably received by the driver handle to threadably drive said suture anchor fully into the bone.

17. A suture anchor system for securing a suture to a bone, said suture anchor system comprising:
   a suture anchor operable to retain a portion of the suture within the bone, said suture anchor including,
      a rigid spear member operable to pierce the bone, said rigid spear member defining a bore laterally passing through the rigid spear member operable to receive a portion of the suture,
      a plurality of wing members extending from said rigid spear member, and
      an impact seat operable to be firmly engaged by said starter plunger and said insertion plunger along an axial center line of said suture anchor;
   a driver handle having a first end and a second end with a bore passing therethrough, said first end operable to receive a portion of said suture anchor;
   a starter plunger having a first head and a first drive member, said second end of said bore operable to receive said first drive member, whereby said starter plunger is operable to drive said suture anchor at least partially into the bone to a first depth; and
   an insertion plunger having a second head and a second drive member, said second end of said bore operable to receive said second drive member, whereby said insertion plunger is operable to drive said suture anchor fully into the bone to a second depth.

18. A suture anchor system for securing a suture to a bone, said suture anchor system comprising:
   a suture anchor operable to retain a portion of the suture within the bone;
   a driving instrument operable to drive the suture anchor into the bone; and
   a resilient retaining member operable to slidably retain the suture relative to the driving instrument, wherein the suture may be slidably removed axially along the driving instrument.

19. The suture anchor system as defined in claim 18 wherein said driving instrument includes a driver handle, a starter plunger, and an insertion plunger.

20. The suture anchor system as defined in claim 18 wherein said suture anchor includes a rigid spear member and an impact seat having a truncated conical shape and an impact base, said driving instrument operable to engage said impact base along an axial centerline of said suture anchor to impact said suture anchor into the bone.

21. The suture anchor system as defined in claim 18 wherein said driving instrument includes a driver handle having a conically shaped finger operable to engage a conically shaped impact seat within said suture anchor to drive said suture anchor into the bone.

22. The suture anchor system as defined in claim 18 wherein said driving instrument includes a driver handle having a first end and a second end with a bore passing therethrough, wherein a portion of said bore is defined by a threaded sidewall.

23. The suture anchor system as defined in claim 18 wherein said driving instrument includes a driver handle and a plunger, said driver handle having a first end and a second end with a bore passing therethrough and a slot extending from said first end, said plunger including a depth control member, wherein said depth control member is operable to be nestingly received within said slot of said driver handle.

24. A method for securing a suture to a bone using a suture anchor, said method comprising the steps of:
   providing a driver handle having a bore passing therethrough;
   positioning a first portion of the suture anchor within the driver handle with a second portion extending out from the driver handle;
   providing a starter plunger which is slidably received within the driver handle to drive at least the second portion of the suture anchor into the bone to a first depth;
   driving at least the second portion of the suture anchor into the bone to the first depth whereby the first portion of the suture anchor substantially remains within the driver handle;
   providing an insertion plunger slidably received within the driver handle to fully drive the first and second portions of the suture anchor into the bone to a second depth; and
   driving the first and second portions of the suture anchor fully into the bone to the second depth.

25. The method as defined in claim 24 further comprising the step of slidably removing the driver handle away from the suture anchor as the suture is slidably removed from under a resilient O-ring.

26. The method as defined in claim 24 wherein the step of driving the first and second portions of the suture anchor fully into the bone further includes the step of threading the insertion plunger within the bore of the driver handle as the insertion plunger is slidably received within the driver handle.

27. The method as defined in claim 26 wherein the step of driving the first and second portions of the suture anchor fully into the bone further includes the step of attaching a securement wire to the driving handle and about the bone.

28. A suture anchor system for securing a suture to a bone, said suture anchor system comprising:

a suture anchor operable to retain a portion of the suture within the bone; and a driving instrument operable to drive the suture anchor into the bone, said driving instrument includes a driver handle having a first end and a second end with a bore passing therethrough, said first end including a counterbore seat operable to receive a portion of said suture anchor, said driving instrument further including a depth control mechanism operable to drive the suture anchor to a first depth within the bone and to a second depth within the bone, whereby a first portion of said suture anchor is driven to said first depth and said first portion and a second portion of said suture anchor are driven to said second depth.

29. The suture anchor system as defined in claim 28 wherein the depth control mechanism includes a starter plunger and an insertion plunger.

30. The suture anchor system as defined in claim 28 wherein the depth control mechanism includes a driver handle having a slot and a plunger having a depth control member operable to be nestingly received within said slot.

31. The suture anchor system as defined in claim 28 wherein the driving instrument includes a plunger having a head and a drive member, said depth control mechanism includes said head and said first end of said driver handle.

32. A suture anchor system for securing a suture to a bone, said suture anchor system comprising:

a suture anchor operable to retain a portion of the suture within the bone;

a driver handle having a first end and a second end with a bore passing therethrough, said first end including a counterbore cavity operable to receive a first portion of said suture anchor; and at least one plunger having a head and a drive member, said second end of said bore operable to receive said drive member, whereby said plunger is operable to drive at least a second portion of said suture anchor into the bone to a first depth, wherein said first portion of the suture anchor substantially remains within said counterbore cavity.

33. The suture anchor system as defined in claim 32 wherein suture anchor includes, a rigid spear member operable to pierce the bone, said rigid spear member defining a bore laterally passing through the rigid spear member operable to receive a portion of the suture, a plurality of wing members extending from said rigid spear member, and an impact seat operable to be firmly engaged by said starter plunger and said insertion plunger along an axial center line of said suture anchor.

34. The suture anchor system as defined in claim 32 wherein said driver handle includes a slot and said at least one plunger includes a depth control member operable to be nestingly received within said slot whereby said suture anchor is operable to be driven to said first depth and to a second depth.

35. The suture anchor system as defined in claim 32 further comprising a second plunger having a head and a drive member, said second end of said bore operable to receive said drive member, whereby said second plunger is operable to drive said first and second portions of said suture anchor to a second depth.

36. A suture anchor system for securing a suture to a bone, said suture anchor system comprising:

a suture anchor operable to retain a portion of the suture within the bone;

a driver handle having a first end and a second end with a bore passing therethrough; and at least one plunger having a head and a drive member, said second end of said bore operable to receive said drive member, said drive member including a drive shaft and a plunger pin, said plunger pin includes at least a first cylindrical sidewall having a first diameter and a second cylindrical sidewall having a second diameter, wherein said plunger is operable to drive said suture anchor at least partially into the bone.

37. A suture anchor system for securing a suture to a bone, said suture anchor system comprising:

a suture anchor operable to retain a portion of the suture within the bone;

a driver handle having a first end and a second end with a bore passing therethrough; and at least one plunger having a head and a drive member, said second end of said bore operable to receive said drive member, said drive member further including a depth control member operable to be received within a slot in said driver handle, whereby said plunger is operable to drive said suture anchor partially into the bone to a first depth with the depth control member engaging said first end of said driver handle and operable to drive said suture anchor fully into the bone to a second depth upon engagement of the depth control member within said slot of said driver handle.

* * * * *

UNITED STATES PATENT AND TRADEMARK OFFICE
CERTIFICATE OF CORRECTION

PATENT NO. : 5,980,558  
DATED : November 9, 1999  
INVENTOR(S) : Roy C. Wiley

Page 1 of 1

It is certified that error appears in the above-identified patent and that said Letters Patent is hereby corrected as shown below:

Column 3,  
Line 8, "illustrates" should be -- illustrate --  
Line 16, "illustrates" should be -- illustrate --  
Line 26, "illustrates" should be -- illustrate --

Column 4,  
Line 66, "then" should be -- than --

Column 5,  
Line 4, "a" should be -- an --

Column 11,  
Line 22, "there between" should be -- therebetween --  
Line 49, "there between" should be -- therebetween --

Signed and Sealed this

Twenty-sixth Day of February, 2002

Attest:

JAMES E. ROGAN  
Attesting Officer    Director of the United States Patent and Trademark Office